US012752108B2

(12) United States Patent
Shanks et al.

(10) Patent No.: US 12,752,108 B2
(45) Date of Patent: Oct. 6, 2026

(54) TISSUE STIMULATING DEVICES, SYSTEMS, AND METHODS

(71) Applicants: Todd Shanks, Dallas, TX (US); George Alexander Jones, River Forest, IL (US); Brent Felix, Salt Lake City, UT (US); Jeremy Heiser, Salt Lake City, UT (US); Ron Groberg, Syracuse, UT (US)

(72) Inventors: Todd Shanks, Dallas, TX (US); George Alexander Jones, River Forest, IL (US); Brent Felix, Salt Lake City, UT (US); Jeremy Heiser, Salt Lake City, UT (US); Ron Groberg, Syracuse, UT (US)

( * ) Notice: Subject to any disclaimer, the term of this patent is extended or adjusted under 35 U.S.C. 154(b) by 1106 days.

(21) Appl. No.: 17/875,275

(22) Filed: Jul. 27, 2022

(65) Prior Publication Data

US 2023/0029611 A1 Feb. 2, 2023

Related U.S. Application Data

(60) Provisional application No. 63/203,588, filed on Jul. 27, 2021.

(51) Int. Cl.
*A61N 1/32* (2006.01)
*A61F 2/28* (2006.01)
(Continued)

(52) U.S. Cl.
CPC ................ *A61N 1/326* (2013.01); *A61F 2/28* (2013.01); *A61F 13/00051* (2013.01);
(Continued)

(58) Field of Classification Search
CPC .. A61N 1/326; A61L 27/08; A61F 2002/2821
See application file for complete search history.

(56) References Cited

U.S. PATENT DOCUMENTS

| | | | |
|---|---|---|---|
| 6,143,035 | A | 11/2000 | McDowell |
| 6,872,403 | B2 | 3/2005 | Pienkowski et al. |

(Continued)

FOREIGN PATENT DOCUMENTS

| | | | |
|---|---|---|---|
| AU | 2011265386 A1 | 1/2012 | |
| BR | PI0903718 A2 | 6/2011 | |

(Continued)

OTHER PUBLICATIONS

International Search Report dated Nov. 10, 2022 for corresponding Application No. PCT/US2022/038583.

(Continued)

*Primary Examiner* — Brian A Dukert
(74) *Attorney, Agent, or Firm* — David Meibos; Maywood IP Law

(57) ABSTRACT

An orthopedic prosthesis for stimulating bone growth may include a substrate having at least one bone-facing surface and at least one internal surface, at least one piezoelectric nanostructure coupled to the at least one bone-facing surface of the substrate, at least one charge storing material placed within the orthopedic prosthesis proximate the at least one internal surface, and an interconnect in electrical communication with the at least one piezoelectric nanostructure and the charge storing material. The at least one piezoelectric nanostructure may be configured to generate an electric charge in response to at least one mechanical force applied to the at least one piezoelectric nanostructure and the interconnect may be configured to transfer the electric charge to the at least one charge storing material to promote bone in-growth within the orthopedic prosthesis and/or on the at least one bone-facing surface.

18 Claims, 8 Drawing Sheets

(51) Int. Cl.

| | |
|---|---|
| ***A61F 13/00*** | (2006.01) |
| ***A61L 27/08*** | (2006.01) |
| *A61F 2/30* | (2006.01) |

(52) U.S. Cl.

CPC ....... *A61L 27/08* (2013.01); *A61F 2002/2821* (2013.01); *A61F 2002/30087* (2013.01); *A61F 2002/3084* (2013.01); *A61F 2013/00089* (2013.01); *A61F 2013/00238* (2013.01); *A61F 2310/00574* (2013.01); *A61L 2400/12* (2013.01); *A61L 2400/18* (2013.01)

(56) References Cited

U.S. PATENT DOCUMENTS

| | | | |
|---|---|---|---|
| 7,431,734 | B2 | 10/2008 | Danoff et al. |
| 8,728,817 | B2 | 5/2014 | Ogle et al. |
| 9,192,912 | B1 | 11/2015 | Mills et al. |
| 10,292,831 | B2 | 5/2019 | Zellmer et al. |
| 10,350,329 | B2 | 7/2019 | Shah et al. |
| 10,617,880 | B2 | 4/2020 | Zellmer et al. |
| 10,960,218 | B2 * | 3/2021 | Friis ...................... A61N 1/378 |
| 2003/0153965 | A1 | 8/2003 | Supronowicz et al. |
| 2007/0198090 | A1 | 8/2007 | Abdou |
| 2011/0224578 | A1 | 9/2011 | Edman et al. |
| 2011/0262501 | A1 | 10/2011 | Webster et al. |
| 2015/0134061 | A1 | 5/2015 | Friis et al. |
| 2020/0297494 | A1 | 9/2020 | Hunt et al. |

FOREIGN PATENT DOCUMENTS

| | | | |
|---|---|---|---|
| WO | 2005120631 | A1 | 12/2005 |
| WO | 2017019863 | A1 | 2/2017 |

OTHER PUBLICATIONS

Khatua et al., “In situ electrical stimulation for enhanced bone growth: A mini-review”, Medical Devices & Sensors, vol. 3, Issue 4 (2020), pp. 1-41.

* cited by examiner

TISSUE STIMULATING DEVICES, SYSTEMS, AND METHODS

CROSS-REFERENCE TO RELATED APPLICATIONS

This application claims the benefit of U.S. Provisional Patent Application Ser. No. 63/203,588 filed on Jul. 27, 2021, entitled "NANOMATERIALS FOR ENHANCED BONE FUSION AND HEALING APPLICATIONS". The foregoing document is hereby incorporated by reference in its entirety.

TECHNICAL FIELD

The present disclosure relates to tissue stimulating devices, systems, and methods. More specifically, the present disclosure relates to devices, systems, and methods for stimulating bone tissue and other tissues to promote growth and healing.

BACKGROUND

The present disclosure describes orthopedic implants or prostheses that may comprise one or more nanomaterials (e.g., carbon nanotubes) on one or more bone-facing surfaces of the orthopedic implants. The present disclosure also describes soft tissue devices or bandages that may comprise one or more nanomaterials that may be placed proximate a soft tissue wound.

The one or more nanomaterials may be configured to generate an electric charge that can stimulate tissue growth and/or healing (e.g., bone tissue growth, soft tissue growth, etc.). Examples nanomaterials may include but are not limited to: carbon nanotubes or tubules, titanium nanotubes, boron carbon and nitrogen nanotubes, boron nitride nanotubes, DNA nanotubes, gallium nitride nanotubes, silicon nanotubes, inorganic nanotubes, tunneling nanotubes, etc.

Compressive forces acting perpendicular to the one or more nanomaterials may cause the one or more nanomaterials to generate an electric charge. Electric charge may also be generated by the one or more nanomaterials via non-perpendicular forces, torsion forces, shear forces, etc., and combinations thereof.

In some embodiments, the orthopedic implants and/or soft tissue devices of the present disclosure may also include an electrically conductive nanoplate or nanosheet (e.g., a graphene sheet) that may be configured and positioned to convey or store electric charge to stimulate bone/tissue growth in the space surrounding or within the orthopedic implant/soft tissue device.

In some embodiments, the orthopedic implants and/or soft tissue devices of the present disclosure may also include a surface coating or nano-coating that may comprise a bioactive, bioabsorbable, and/or biodegradable material.

SUMMARY

The various devices, systems, and methods of the present disclosure have been developed in response to the present state of the art, and in particular, in response to the problems and needs in the art that have not yet been fully solved by currently available devices, systems, and methods. In some embodiments, the tissue stimulating devices, systems, and methods of the present disclosure may provide improved tissue growth/healing.

In some embodiments, an orthopedic prosthesis for stimulating bone growth may include a substrate having at least one bone-facing surface and at least one internal surface, at least one piezoelectric nanostructure coupled to the at least one bone-facing surface of the substrate, at least one charge storing material placed within the orthopedic prosthesis proximate the at least one internal surface, and an interconnect in electrical communication with the at least one piezoelectric nanostructure and the charge storing material. The at least one piezoelectric nanostructure may be configured to generate an electric charge in response to at a least one mechanical force applied to the at least one piezoelectric nanostructure and the interconnect may be configured to transfer the electric charge to the at least one charge storing material to promote bone in-growth within the orthopedic prosthesis and/or on the at least one bone-facing surface.

In some embodiments, the at least one piezoelectric nanostructure may include at least one nanotube.

In some embodiments, the at least one nanotube may include at least one carbon nanotube.

In some embodiments, the at least one nanotube may include a plurality of nanotubes projecting from the at least one bone-facing surface and oriented substantially parallel with each other.

In some embodiments, the interconnect may include a graphene nanosheet.

In some embodiments, the at least one charge storing material may include carbon.

In some embodiments, the orthopedic prosthesis may be configured to experience the at least one mechanical force while the orthopedic prosthesis is implanted within a patient.

In some embodiments, an orthopedic prosthesis for stimulating bone growth may include substrate having at least one bone-facing surface, a first piezoelectric nanostructure coupled to the at least one bone-facing surface at a first location, a second piezoelectric nanostructure coupled to the at least one bone-facing surface at a second location, and a conductor electrically coupled with the first piezoelectric nanostructure and the second piezoelectric nanostructure. The first piezoelectric nanostructure may be configured to generate a first electric charge in response to a first mechanical force applied to the first piezoelectric nanostructure. The second piezoelectric nanostructure may be configured to generate a second electric charge in response to a second mechanical force applied to the second piezoelectric nanostructure. The conductor may be configured to transfer the first electric charge to the second piezoelectric nanostructure and transfer the second electric charge to the first piezoelectric nanostructure to promote bone growth on at least one of the first location and the second location of the at least one bone-facing surface.

In some embodiments, at least one of the first piezoelectric nanostructure and the second piezoelectric nanostructure may include a nanotube.

In some embodiments, the nanotube may include a carbon nanotube.

In some embodiments, wherein the nanotube may include a plurality of nanotubes projecting from the at least one bone-facing surface and oriented substantially parallel with each other.

In some embodiments, the conductor may include a graphene nanosheet.

In some embodiments, the orthopedic prosthesis may be configured to experience at least one mechanical force while the orthopedic prosthesis is implanted within a patient.

In some embodiments, an orthopedic prosthesis for stimulating bone growth may include a substrate having a first bone-facing surface and a second bone-facing surface, opposite the first bone-facing surface, a first piezoelectric nanostructure coupled to the first bone-facing surface, a second piezoelectric nanostructure coupled to the second bone-facing surface, and at least one interconnect in electrical communication with at least one of the first piezoelectric nanostructure and the second piezoelectric nanostructure. The first piezoelectric nanostructure may be configured to generate a first electric charge in response to a compression force applied to the first piezoelectric nanostructure. The second piezoelectric nanostructure may be configured to generate a second electric charge in response to the compression force applied to the second piezoelectric nanostructure. The at least one interconnect may be configured to transmit at least one of the first electric charge and the second electric charge to promote bone growth on at least one of the first bone-facing surface and the second bone-facing surface.

In some embodiments, at least one of the first piezoelectric nanostructure and the second piezoelectric nanostructure may include a nanotube.

In some embodiments, the nanotube may include a carbon nanotube.

In some embodiments, the nanotube may include a plurality of nanotubes oriented substantially parallel with each other and projecting from at least one of the first bone-facing surface and the second bone-facing surface.

In some embodiments, the interconnect may include a graphene nanosheet.

In some embodiments, the orthopedic prosthesis may be configured to experience the compression force while the orthopedic prosthesis is implanted within a patient.

In some embodiments, the at least one interconnect may be in electrical communication with the first piezoelectric nanostructure coupled to the first bone-facing surface and the second piezoelectric nanostructure coupled to the second bone-facing surface, the at least one interconnect may extend between the first bone-facing surface and the second bone-facing surface, and the at least one interconnect may be configured to transmit at least one of the first electric charge and the second electric charge between the first bone-facing surface and the second bone-facing surface to promote bone growth on at least one of the first bone-facing surface and the second bone-facing surface.

In some embodiments, a soft tissue device for stimulating tissue growth may include a flexible mesh having a plurality of piezoelectric fibers interwoven with each other to form the flexible mesh and a tissue-facing surface of the flexible mesh in electrical communication with a wound of a patient. The flexible mesh may be couplable to skin of the patient proximate the wound. The plurality of piezoelectric fibers may be configured to generate an electric charge in response to at least one mechanical force applied to the plurality of piezoelectric fibers via movement of the skin relative to the flexible mesh. The tissue-facing surface of the flexible mesh may be configured to transmit the electric charge to the wound to stimulate tissue growth and promote healing of the wound.

In some embodiments, the plurality of piezoelectric fibers may include nanotube fibers.

In some embodiments, the nanotube fibers may include carbon fiber yarns.

In some embodiments, the flexible mesh may be coupled to a pliable sheet of the soft tissue device.

In some embodiments, the pliable sheet comprising the flexible mesh may be couplable to skin of the patient proximate the wound.

In some embodiments, the soft tissue device may further include an interconnect in electrical communication with the plurality of piezoelectric fibers and configured to convey the electric charge to the wound.

In some embodiments, the interconnect may include a graphene nanosheet.

These and other features and advantages of the present disclosure will become more fully apparent from the following description and appended claims or may be learned by the practice of the tissue stimulating devices, systems, and methods set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which.

Figure 1A:
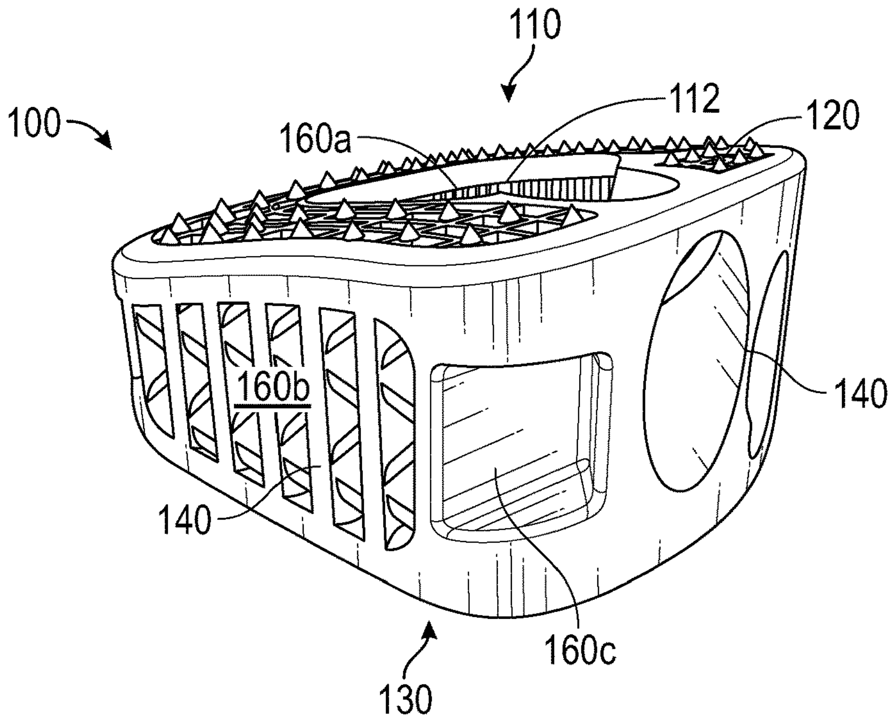
FIG. 1A is a perspective view of an orthopedic prosthesis, according to an embodiment of the present disclosure.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the devices, systems, and methods, as represented in the drawings, is not intended to limit the scope of the present disclosure but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. Varus means deviation of the distal part of the leg below the knee inward, resulting in a bowlegged appearance. Valgus means deviation of the distal part of the leg below the knee outward, resulting in a knock-kneed appearance.

As used herein, the term "nanomaterial" refers to a material of which a single unit has a small size (in at least one dimension) between 1 and 100 nanometers, also referred to as nanoscale. Materials with a structure at the nanoscale may have unique optical, electronic, thermo-physical or mechanical properties. The term nanomaterial may also include material defined by the ISO/TS 80004 standard as "material with any external dimension in the nanoscale or having internal structure or surface structure in the nanoscale", with nanoscale defined as the "length range approximately from 1 nm to 100 nm." This may include both nano-objects, which are discrete pieces of material, and nanostructured materials, which may have internal or surface structure on the nanoscale. Thus, a nanomaterial may be a member of both these categories. Nanomaterial may be specifically engineered, occur naturally, or be created as an incidental byproduct of another mechanical or industrial process. Nano-objects are often categorized based on how many of their dimensions fall in the nanoscale. A nanoparticle may be defined as a nano-object with all three external dimensions in the nanoscale, having a longest and shortest axis that may not differ significantly. A nanofiber may have two external dimensions in the nanoscale, with nanotubes being hollow nanofibers and nanorods being solid nanofibers. A nanoplate/nanosheet may have one external dimension in the nanoscale, and if the two larger dimensions are significantly different it may be referred to as a nanoribbon. For nanofibers and nanoplates, the other dimensions may or may not be in the nanoscale but may be significantly larger. A difference in dimensions may be considered significant if the difference is at least a factor of three. Nanostructured materials can be categorized by what phases of matter they contain. A nanocomposite may be a solid containing at least one physically or chemically distinct region, or collection of regions, having at least one dimension in the nanoscale. A nanofoam may have a liquid or solid matrix filled with a gaseous phase, where one of the two phases has dimensions on the nanoscale. A nano-porous material may be a solid material containing nanopores or voids in the form of open or closed pores at sub-micron length scales. A nanocrystalline material may have a significant fraction of crystal grains in the nanoscale.

As used herein, the terms "prosthesis" or "implant" may refer to a medical device manufactured to replace a missing biological structure, support a damaged biological structure, or enhance an existing biological structure. Medical prostheses/implants may be man-made devices. The surface of implants that contact the body may be made of biocompatible/bioactive materials such as titanium, silicone, apatite, etc. Orthopedic implants may be used to alleviate issues with bones and/or joints of a patient's body. Orthopedic implants may be used to treat bone fractures, osteoarthritis, scoliosis, spinal stenosis, chronic pain, etc. Examples of orthopedic implants include, but are not limited to, spacers, cages, pins, rods, screws, anchors, plates, stems, surface interfaces, dental implants, oral/maxillofacial implants, etc.

As used herein, "osteoinductive" refers to a type or kind of material, device, structure, or apparatus that stimulates cells of a patient to grow bone tissue.

As used herein, "substrate" refers to any material that provides a surface on which something may be deposited, inscribed, or constructed. A substrate may include any surface modification. Examples include, but are not limited to: media blasting, etching, plasma modifications, seeding, surface coating, nano-coating, etc. A substrate may be a solid, rigid, lattice, or flexible structure and may be planar or curved in shape. A substrate may also be used in a variety of structures including medical implants. A substrate may be non-conductive, semi-conductive, or conductive, and may be formed from a variety of materials including plastic, ceramics, metal, acrylic, carbon, and biodegradable materials, stainless steel, titanium, titanium composite/alloy, cobalt chrome, tantalum, silicon nitride, polyetheretherketone, poly (ε-caprolactone), polyurethane, allograft, Poly-VD-lactic acid (PLDLA), silicon, resin, fiberglass, silicon dioxide, aluminum oxide, sapphire, germanium, gallium arsenide (GaAs), an alloy of silicon and germanium, indium phosphide (InP), etc. In certain embodiments, a substrate may comprise a surface of a medical implant. In certain embodiments, a substrate may comprise a base layer of a body fora medical implant. In certain embodiments, a substrate may comprise a silicon wafer and in other embodiments, a substrate may comprise another layer of an integrated semiconductor, including, but not limited to, a top surface of a cell film stack, or the like.

As used herein, the term "allograft" may refer to a type of tissue and/or organ graft in which the tissue or organ of the graft is from a donor of the same species (but not necessarily the same genotype). Bone grafts may be of an allograft type of a mixture of other graft types including allograft, autograft, and xenograft. Autograft refers to a type of tissue and/or organ graft in which the tissue or organ of the graft is from the patient. Xenograft refers to a type of tissue and/or organ graft in which the tissue or organ of the graft is from a donor of another species.

As used herein, an "opening" or "void" may refer to a gap, a hole, an aperture, a space or recess in a structure, an opening in a structure, etc. In certain embodiments, a void can refer to a structure configured specifically for receiving something and/or for allowing access. In some embodiments, a void may pass through a structure. In some embodiments, a void may exist within a structure but not pass through the structure.

As used herein, a "mesh" may refer to a two or three dimensional planar structure that may have a plurality of openings distributed within a longitudinal plane of the structure. Each of the plurality of openings of the mesh may be of a common shape or a random shape. Alternatively, or in addition, the plurality of openings of the mesh may include openings having two or more geometric shapes.

As used herein, "osteoconductive" may refer to a type or kind of material, device, structure, substrate, or apparatus that may provide a suitable scaffold or matrix upon which bone tissue can grow.

As used herein, "osteogenic" may refer to a type or kind of material that stimulates bone growth and/or osteoblast/mesenchymal cells. In some embodiments, when the nanomaterials described or contemplated herein generate and/or hold an electric charge, greater bone and/or osteoblast/mesenchymal cell migration, colonization, differentiation, and/or growth may occur.

As used herein, a "fixator" refers to an apparatus, instrument, structure, device, component, member, system, assembly, or module structured, organized, configured, designed, arranged, or engineered to connect two bones or bone fragments or a single bone or bone fragment and another fixator to position and retain the bone or bone fragments in a desired position and/or orientation. Fixators can also serve to redistribute load and stresses experienced by bone(s) and/or body parts and can serve to reduce relative motion of one part relative to others. Examples of fixators include both those for external fixation as well as those for internal fixation and include, but are not limited to pins, wires, Kirschner wires, screws, anchors, bone anchors, plates, bone plates, intramedullary nails/rods/pins, implants, interbody cages, fusion cages, etc.

As used herein, a "coating" refers to a layer or covering of a structure. The structure may be a substrate, a base layer, another layer, or any object. The coating may be solid, semi-solid, and/or amorphous either when applied or after a drying or curing period. The coating may include a single element, a set of single elements forming a molecule, one or more compounds, or a mixture. A coating may have a variety of thicknesses and the thicknesses may be uniform or non-uniform across a surface and/or substrate. The coating may have a nano-scale thickness, a micro-scale thickness, a macro-scale thickness, or a combination of these. A coating may be applied by painting, spraying, pouring, immersion within the coating, and the like. "Layer" may refer to a planar set of material in a multilayer structure.

As used herein, "electrical communication" may refer to a circuit, connection, contact, lead, trace, path, or relationship between two structures that may be configured, designed, coordinated, or organized to pass, convey, transfer, transmit or send an electric charge, charge carrier, or current between a source and a destination. Examples of electrical communication may include, but are not limited to, a conductor or interconnect between a source and a destination that passes an electric charge, charge carrier, or current through or on a surface of the conductor or interconnect, a conductor or interconnect in proximity to a magnetic, static, or electrical field, that causes a movement of electric charge within the conductor or interconnect, etc.

Piezoelectricity is the ability of a material to generate electrical activity in response to an applied mechanical force/stress. In piezoelectric materials, stress-generated deformation produces an asymmetric shift of ions or charges to create electric polarization and/or an electrical charge in the piezoelectric material. Bone is a piezoelectric material which originates due to movement of collagen fibers under mechanical force/stress.

As used herein, "piezoelectric nanostructure" may refer to any nanostructure that exhibits piezoelectric activity. Example piezoelectric nanostructures include, but are not limited to: nanotubes, nanosheets, nanoballs, fullerenes, crystal/crystalline structures, allotropes, etc.

As used herein, "charge storing material" may include any material that is at least partially conductive that can dissipate, transfer, and/or store an electric charge over any length of time.

Although the orthopedic prostheses described herein are disclosed in the context of spinal cages, it will be readily understood by those of skill in the art that the inventive concepts described and contemplated herein may be applied to any orthopedic prosthesis for any bone or joint of a patient or an animal, including, but not limited to, bones/joints of the foot, ankle, knee, hip, hand, wrist, elbow, shoulder, sacral, spine, neck, teeth, skull, etc., without departing from the spirit or scope of the present disclosure.

It will also be understood that any component or feature of any orthopedic prosthesis or soft tissue device that is described or contemplated herein may be combined with any other component or feature that is described or contemplated herein to create any number of different orthopedic prosthesis and/or soft tissue device embodiments.

It will also be understood that any component or feature of any orthopedic prosthesis or soft tissue device described or contemplated herein may be combined with any other component or feature that is described or contemplated herein to create any number of different surgical kits. Each of these surgical kits may also include (or not include) any number of supporting surgical instruments or general parts (e.g., bone screws, fasteners, K-wires, medical tape, sutures, etc.).

Moreover, it will also be understood that any method step (or component/feature of any method step) that is described or contemplated herein may be combined with any other method step (or component/feature of any method step) that is described or contemplated herein in any order, and/or in any combination, to create any number of different method embodiments for implanting or securing any number of different orthopedic prosthesis and/or soft tissue device embodiments that are described or contemplated herein.

FIG. 1A illustrates an orthopedic prosthesis 100 that may be utilized with one or more tissue stimulating structures discussed herein, according to an example of the present disclosure. The orthopedic prosthesis 100 may be any prosthesis such as a cage, a spacer, a plate, a rod, a screw, or any implant that may experience a load or strain when implanted in a patient.

In the illustrated embodiment, the orthopedic prosthesis 100 is a fusion cage 110 (also referred to as an "intervertebral fusion cage," "interbody cage," or "intervertebral cage") used in connection with a spinal arthrodesis procedure to fuse adjacent vertebrae to each other via bony in-growth between the vertebrae (e.g., within an intervertebral space between the adjacent vertebrae). During the healing period and interbody bone growth, the fusion cage may provide structural support against load forces transmitted between the adjacent vertebrae. Quick and complete bone growth within the intervertebral space and around/within the fusion cage can result in a successful outcome for the patient.

Various techniques may be utilized to encourage and promote bone growth within the interbody space and around/within the fusion cage. Such techniques may include a bone graft material (such as allograft, autograft, or xenograft bone graft material) within or around the fusion cage and/or within the interbody space between the vertebrae. The fusion cage and/or bone graft material may be osteoconductive, osteoinductive, and/or osteogenic. In certain embodiments, the fusion cage 110 may include at least one opening, space, or void 112 within the fusion cage 110. The void 112 may be configured to receive a bone graft material. In this manner, the fusion cage 110 can serve as a container for bone graft material to encourage and accelerate bone growth between two vertebrae.

In some embodiments, the fusion cage 110 may include a superior surface 120, an inferior surface 130, and one or more sides 140. The fusion cage 110 may be one type of fixator.

In some embodiments, the sides 140, the superior surface 120, and/or the inferior surface 130 may be solid or include a plurality of openings or voids. Openings in the sides 140, the superior surface 120, and/or the inferior surface 130 may encourage bone growth around/within the fusion cage 110. Promoting bone growth within the fusion cage 110 may be challenging. However, aspects of the present disclosure can ameliorate this issue, as will be discussed below in more detail.

Each of the superior surface 120, the inferior surface 130, and the one or more sides 140 may comprise bone-facing surfaces. Typically, the superior surface 120 and inferior surface 130 comprise bone-facing surfaces inserted between adjacent vertebrae. The one or more sides 140 may also be bone-facing surfaces depending on the application in which the fusion cage 110 is utilized and how the fusion cage 110 is oriented with respect to the bones of the patient.

Each of the superior surface 120, the inferior surface 130, and the one or more sides 140 may include or be formed from a substrate. In certain embodiments, the superior surface 120, the inferior surface 130, the one or more sides 140, and/or one or more surfaces of the one or more voids may each or separately include a coating or layer of a material. In some embodiments, the coating may serve an osteoinductive and/or osteogenic function. In some embodiments, the coating may include a single nanomaterial, a compound or mixture of one or more nanomaterials, and/or a mixture of one or more nanomaterials and one or more other molecules and/or compounds.

Figure 1B:
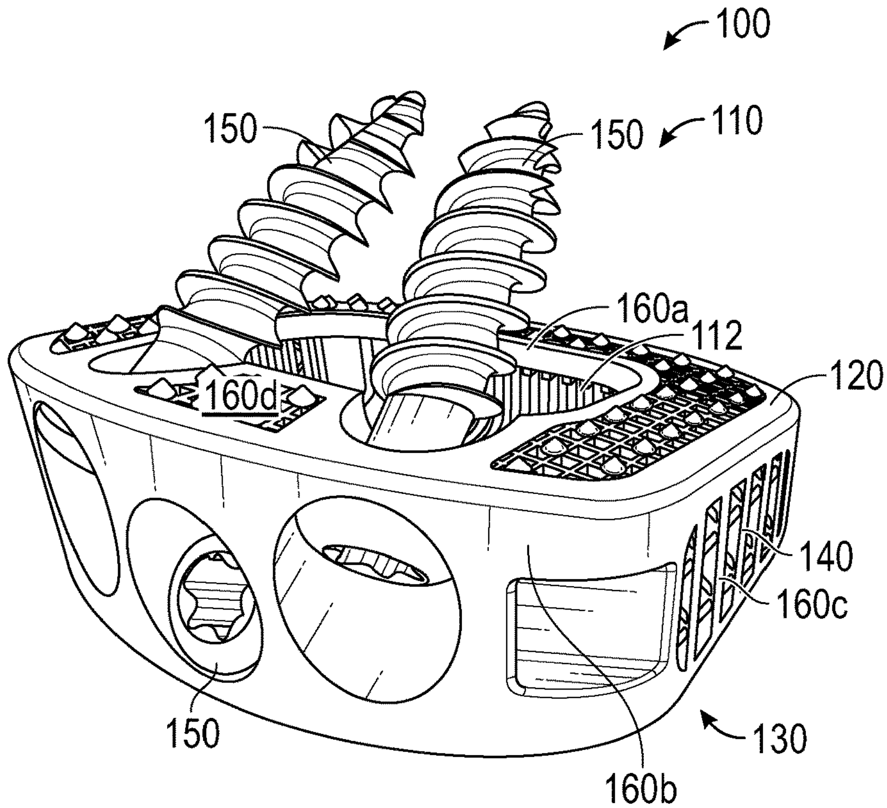
FIG. 1B is a perspective view of an orthopedic prosthesis, according to another embodiment of the present disclosure.

In some embodiments, the fusion cage 110 may include a portion. As used herein, the term "portion" may include any part, segment, section, area, or point within, upon, below, above, on, or inside the fusion cage 110 or one of its components. In some embodiments, the portion may include an area of, or within, the fusion cage 110 where osteoinductive and/or osteogenic growth may be desired. For example, the portion may be a portion that is internal to the orthopedic prosthesis 100. In one embodiment, the portion may be a void or space partially or completely surrounded by the orthopedic prosthesis 100 or fusion cage 110. FIGS. 1A and 1B illustrate different example non-limiting portions 160*a*, 160*b*, 160*c*, and 160*d* that may be in electrical communication with a nanomaterial by way of an interconnect, as will be discussed below in more detail.

FIG. 1B illustrates a perspective view of an orthopedic prosthesis 100 or fusion cage 110 that may be utilized with one or more tissue stimulating structures discussed herein, according to another example of the present disclosure. The fusion cage 110 includes similar aspects to those described in relation to FIG. 1A. In addition, FIG. 1B illustrates one or more anchors 150 or bone screws. The one or more anchors 150 may be utilized to secure the fusion cage 110 to an inferior and/or a superior vertebrae.

Figure 1C:
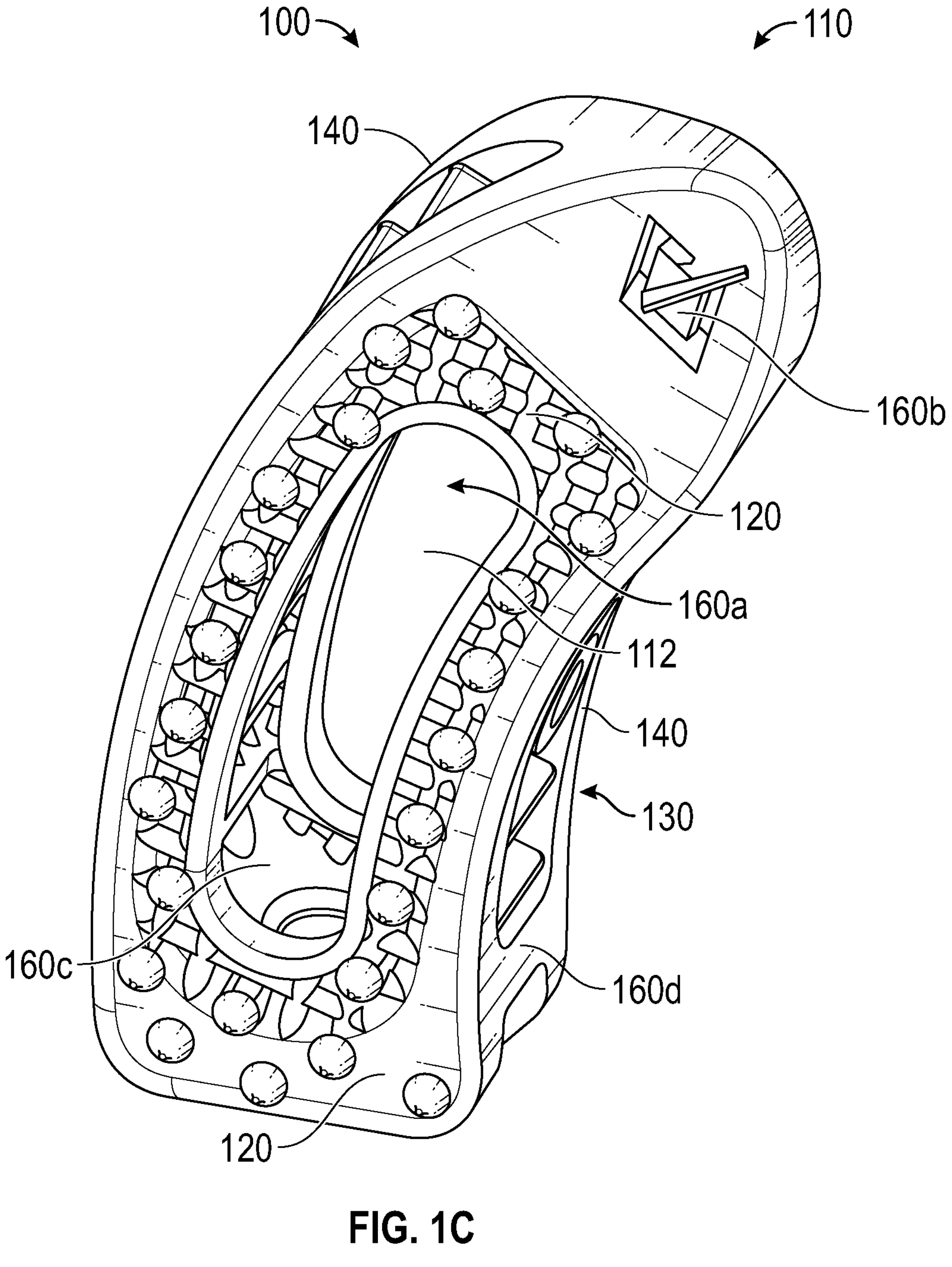
FIG. 1C is a perspective view of an orthopedic prosthesis, according to another embodiment of the present disclosure.

FIG. 1C illustrates a perspective view of another orthopedic prosthesis 100 or fusion cage 110 that may be utilized with one or more tissue stimulating structures discussed herein, according to another example of the present disclosure. The fusion cage 110 includes similar aspects to those described in relation to FIGS. 1A and 1B. The fusion cage 110 comprises a curved shape that may facilitate implantation of the fusion cage 110 from a lateral direction. As with FIGS. 1A and 1B, the fusion cage 110 may include a void 112, a superior surface 120, an inferior surface 130, one or more sides 140, etc.

Figure 2:
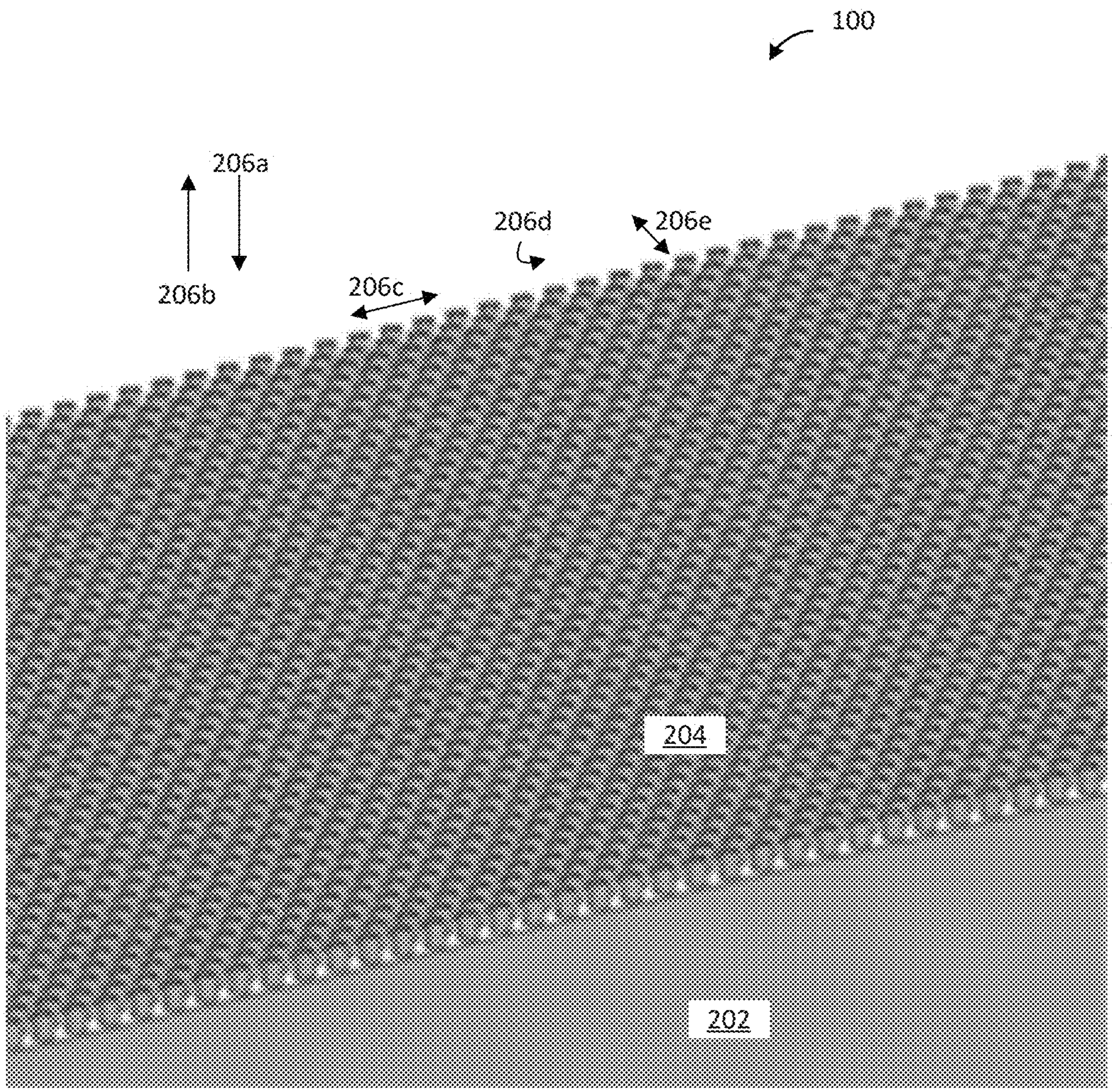
FIG. 2 is a perspective view of a substrate with nanotube structures, according to an embodiment of the present disclosure.

FIG. 2 is a perspective view of a portion of an orthopedic prosthesis 100 comprising a substrate 202 and coating 204, according to an embodiment of the present disclosure.

In some embodiments, the substrate 202 may be planar and smooth or may include various contours and one or more features formed in or connected to the substrate 202. In some embodiments, the substrate 202 and or the coating 204 may comprise a bone-facing surface and the substrate 202 may be shaped in a manner that may maximize an area of the substrate 202 that contacts a bone of a patient placed adjacent the substrate 202. In some embodiments, the substrate 202 may comprise a bone-facing surface that directly contacts a superior or inferior vertebrae of a patient. For example, the substrate 202 may comprise the superior surface 120 and/or the inferior surface 130 of the fusion cage 110.

In some embodiments, the coating 204 may comprise a nanomaterial. In some embodiments, the nanomaterial may comprise a biocompatible material such as carbon, titanium, a titanium alloy, a composite mixture of a nanomaterial and at least one other element, nanotubes, etc.

In some embodiments, the nanotubes may comprise an array of nanotubes. In some embodiments, the array of nanotubes may include nanotubes organized in a uniform distribution (e.g., roughly, or substantially parallel with each other), a random distribution, or combinations thereof. For example, the nanotubes of the coating 204 shown in FIG. 2 are shown extending from the substrate 202 and organized in a uniform distribution generally parallel with each other.

In some embodiments, a plurality of nanotubes may project from at least one bone-facing surface of the orthopedic prosthesis and may be oriented parallel with each other.

In some embodiments, a plurality of nanotubes may project from at least one bone-facing surface of the orthopedic prosthesis and may be oriented substantially parallel with each other. For example, in some embodiments the plurality of nanotubes may be generally or substantially oriented parallel to within +/−30 degrees of each other, +/−20 degrees of each other, +/−10 degrees of each other, +/−5 degrees of each other, etc.

However, it will also be understood that in some embodiments a coating comprising a plurality of nanotubes may be applied or coupled to at least one bone-facing surface of the orthopedic prosthesis. In these embodiments, the plurality of nanotubes may be randomly oriented with respect to each other throughout the coating.

Figure 3A:
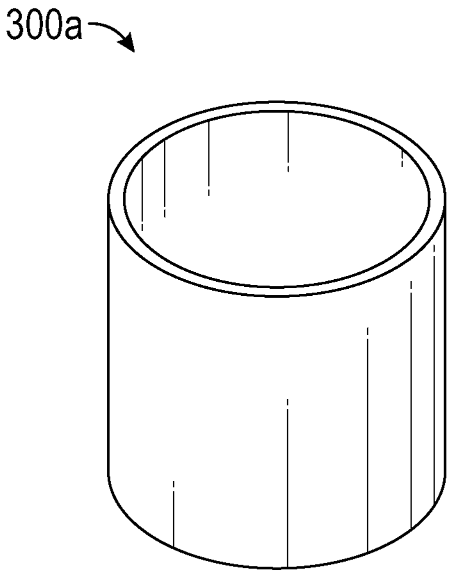
FIG. 3A-3C are perspective views of nanotube structures, according to embodiments of the present disclosure.
Figure 3B:
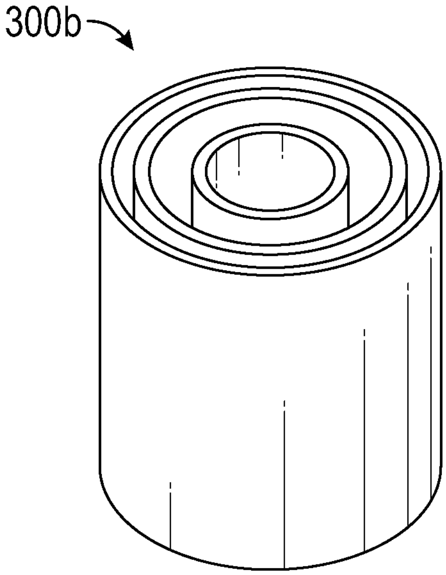
Figure 3C:
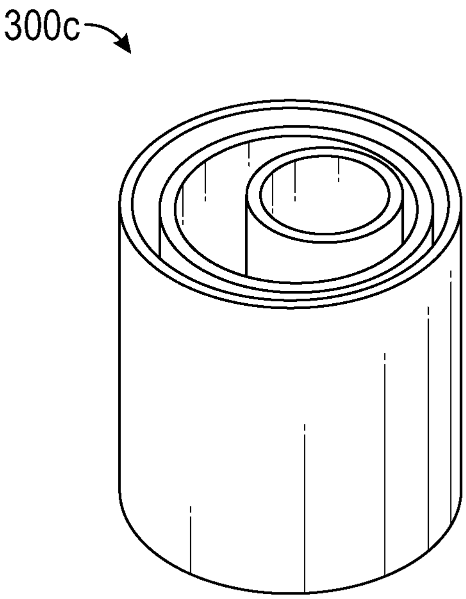

Continuing with FIG. 2, in some embodiments the coating 204 may comprise carbon nanotubes (CNT). A CNT is a tube-like structure made of carbon atoms. A single-wall carbon nanotube (SWCNT) may comprise a single CNT, as shown in FIG. 3A. A Multi-wall carbon nanotube (MWCNT) may comprise two or more nested SWCNTs, as shown in FIGS. 3B and 3C. However, it will be understood that other types of nanomaterials may also be utilized, as discussed herein (e.g., Titanium nanotubes (TiNTs), etc.).

Nanotubes can have piezoelectric properties such that a mechanical force applied to a nanotube can generate an electric charge within the nanotube. For example, some CNTs have been shown to induce a charge of about 48 mC/m2. As shown in FIG. 2, example mechanical forces may be applied to the CNTs of the coating 204. These example mechanical forces may include a compression force 206*a*, a tension force 206*b*, a shear force 206*c*, a torsion force 206*d*, and/or a bending force 206*e*. In a particular example, the CNTs of the coating 204 on the bone-facing surface of the orthopedic prosthesis 100 may experience a cyclic compression load force in the context of a fusion cage 110 implanted within a patient's spine as the patient walks. This mechanical compression force can generate electrical charge within the CNTs of the coating 204 to stimulate bone growth on/within the bone-facing surface of the orthopedic prosthesis 100.

Furthermore, nanotubes may also be utilized to store electric charge and then supply this electric charge once the orthopedic prosthesis 100 is implanted within a patient. For example, certain single element nanotubes may be pre-charged before (or after) being placed on or within an orthopedic prosthesis 100. In certain tests, titanium nanotubes were pre-charged to increase a charge density on, among, and within, the nanotubes. The titanium nanotubes received a charge of 37.15+/−14 mC/cm2. The titanium nanotubes were then used in tests to measure osteoinduction effectiveness (i.e., cell migration and differentiation). The titanium nanotubes were shown to hold four times more charge than materials such as ceramics (e.g., hydroxyapatite). Accordingly, the inventors expect that carbon nanotubes may exhibit similar charge holding/storing capabilities. In certain embodiments, a mixture that includes both titanium nanotubes (either pre-charged or not) and/or carbon nanotubes (either pre-charged or not) may be utilized together in a coating and/or within a void of an implant to provide either a charge source and/or a charge interconnect which may serve to convey charge between structures of an implant and/or an implant site.

In addition, nanotubes, and single element nanotubes in particular, can store electric charge, acting as capacitors. For example, titanium nanotubes have been shown to store a charge that is 0.97 mF/cm2, similar to that of supercapacitors.

In some embodiments, the CNTs may be arranged such that one end of a CNT contacts the substrate 202 and one end of the CNT is free, with the CNTs oriented generally parallel with each other. Such an arrangement may be accomplished utilizing sound waves to sonicate the CNTs during manufacture. Arrays of CNTs can also be manufactured by template-based chemical vapor deposition (CVD). In some embodiments, electric charge generated by the CNTs may accumulate between the CNTs and the substrate 202. The electric charge may be osteoinductive and/or osteogenic for bone growth.

In some embodiments, bone growth may be promoted more readily due to negative electrical charges versus positive electrical charges. Accordingly, the CNTs may be configured to generate negative electrical charges more readily. Such an aspect may be accomplished based on the type of CNTs utilized and/or a combination of types of CNTs utilized. In some embodiments, the CNTs may include metallic CNTs, semiconducting CNTs, or combinations thereof. Alternatively, or in addition thereto, the CNTs may comprise armchair CNTs, zigzag CNTs, chiral CNTs, or combinations thereof.

In some embodiments, parallel aligned nanotubes with one end free and the other end connected to the substrate 202 may increase the surface area of the substrate 202 and/or the bone-facing surface. This increased surface area may be osteoinductive and/or osteogenic to promote bone growth. This higher specific surface area may facilitate a higher contact area, and the ordered array of the nanotubes may also reduce disturbances from inter-particle connections to further promote bone growth.

FIG. 3A-3C show perspective views of nanotube structures 300*a*, 300*b*, 300*c*. FIG. 3A illustrates a single walled carbon nanotube (SWNT), as previously described. In some embodiments, the SWNT may comprise a diameter that is less than about 50 nm. In some embodiments, the SWNT may comprise a diameter that is less than about 100 nm. In some embodiments, the SWNT may comprise a diameter that is less than about 500 nm. However, it will be understood that the SWNT may comprise any diameter or range of diameters.

FIGS. 3B and 3C illustrate examples of a multi-walled nanotube (MWNT), as previously described. The MWNT may comprise one or more SWNTs nested in an arrangement wherein one or more smaller diameter SWNT may be positioned inside one or more larger diameter SWNTs. This nesting arrangement may be concentric (e.g., see FIG. 3B), non-concentric (e.g., see FIG. 3C), or any combinations thereof. Multiples walls of the MWNT may have equal lengths or may be of unequal lengths relative to each other. In some embodiments, the MWNT may comprise an overall diameter that is less than about 50 nm. In some embodiments, the MWNT may comprise an overall diameter that is less than about 100 nm. In some embodiments, the MWNT may comprise an overall diameter that is less than about 500 nm. However, it will be understood that the MWNT may comprise any diameter or range of diameters.

Referring to FIG. 2, in some embodiments the nanotube structures can have a length to diameter ratio of about 1000. In some embodiments, the CNTs of the coating 204 have a uniform or substantially uniform length. In some embodiments, the CNTs or types of CNTs of the coating 204 may have a variety of predefined or random lengths.

In some embodiments, one or more nanotubes of the nanomaterial may extend through the substrate 202 such that an inferior end of the nanotube extends past an inferior surface of the substrate 202 (such as inferior surface 130 or superior surface 120) and a superior end of the nanotube may extend past a superior surface of the substrate 202 (such as inferior surface 130 or superior surface 120). Nanotubes of the nanomaterial may be positioned internal to, or within, a loadbearing substrate (e.g., substrate 202) and/or contained within a non-loadbearing element.

In certain embodiments, one or more nanotubes of the nanomaterial may include a surface coating and/or a nano-coating. Examples coatings may include but are not limited to: collagen, hydroxyapatite (HA), calcium phosphate, calcium phosphate, calcium silicate, glass ceramics, carbon fiber, ionic metals, bioactive material(s), bioabsorbable material(s), etc.

In some embodiments, additional materials (e.g., HA, nanoparticles, ionic metals, etc.) may be added to the nanomaterials described or contemplated herein with no/little change (or possible enhancement) of the electrical and structural properties of the nanomaterials described or contemplated herein.

In certain embodiments, one or more nanotubes of the nanomaterial may be filled, or partially filled, with a drug, ionic metal, charge storing material, bioabsorbable element(s) and/or molecule(s), etc. Examples may include, but are not limited to: small molecule therapeutic drugs, human growth factors, nucleic acids, proteins, F, Ag, Sr, Mg, Zn, $CO_3$, etc.

Figure 4:
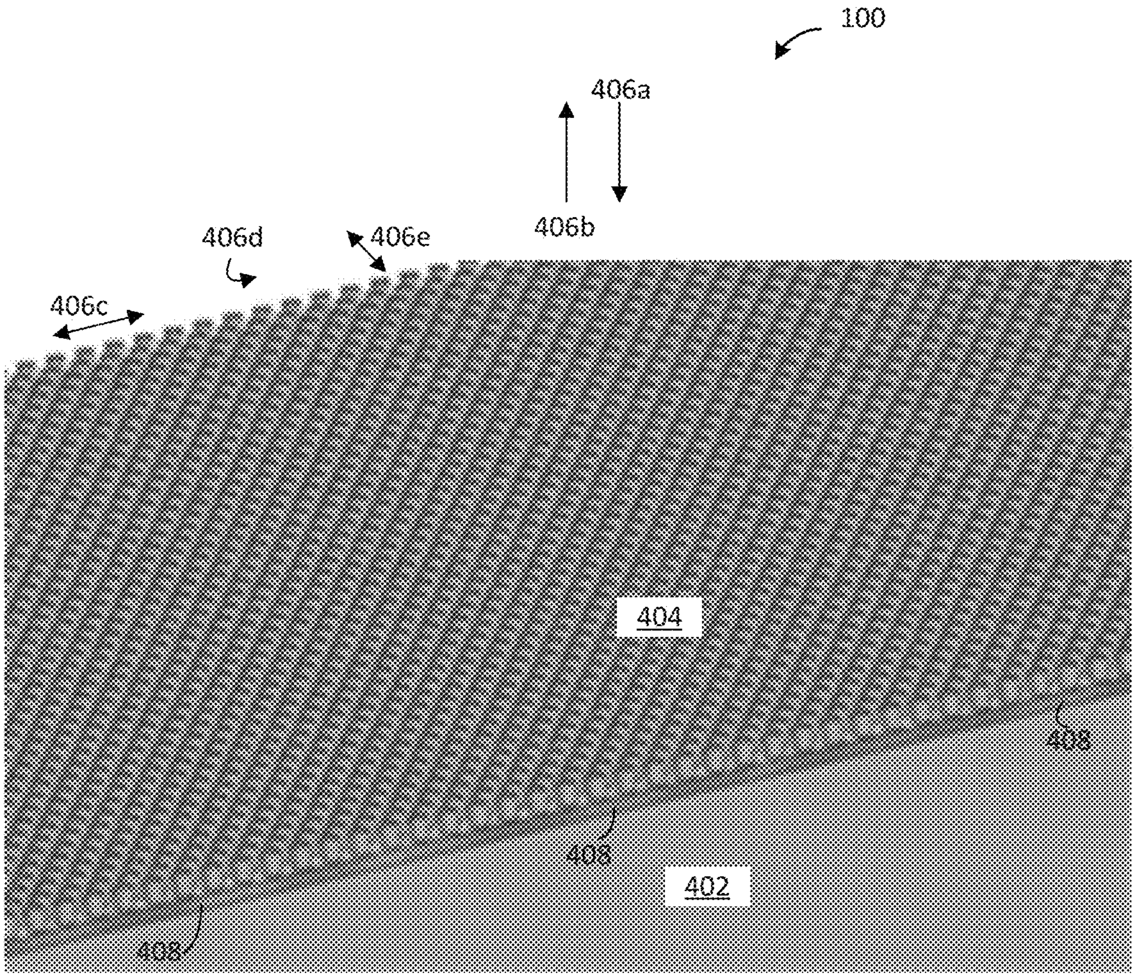
FIG. 4 is a perspective view of a substrate with nanotube structures and an interconnect, according to another embodiment of the present disclosure.

FIG. 4 is a perspective view of a portion of an orthopedic prosthesis 100 comprising a substrate 402, a coating or nanomaterial that may comprise nanotube structures 404, and an interconnect 408, according to another embodiment of the present disclosure. The orthopedic prosthesis 100 may also be subject to mechanical forces 406*a*, 406*b*, 406*c*, 406*d*, and 406*e*, similar those forces described in relation to FIG. 2.

The interconnect 408 may serve to convey, transmit, carry, or transfer electric charge, or electric current from a charge source to another location on, near, around, or within the substrate 402 and/or a feature of or related to the substrate 402, such as a void 112. The interconnect 408 can be made from a variety of materials and configured in a variety of structures. In some embodiments, the interconnect 408 may be a layer of graphene positioned between the nanotube structures 404 and the substrate 402. In some embodiments, the graphene may be configured as a nanoplate or nanosheet. The interconnect 408 (e.g., graphene nanosheet in some embodiments) may be in physical contact and/or electrical communication with the nanotube structures 404 and/or the substrate 402. In some embodiments, the interconnect 408 may include a coating in addition to, or as an alternative to, a coating used with an implant. In some embodiments, the interconnect coating may be applied to the nanotube structures 404 and/or one or more of the substrate surfaces. Such a coating on the interconnect 408 may be similar to other coatings described herein. In some embodiments, the interconnect 408 may be coupled to the substrate 402 before the nanotube structures 404 are coupled to the interconnect 408.

Alternatively, or in addition thereto, the interconnect 408 may comprise a layer coupled to the nanotube structures 404 such that nanomaterial of the nanotube structures 404 may be surrounded by the interconnect 408 with one end of the nanomaterial contacting the substrate 402. In some embodiments, the nanotube structures 404 and interconnect 408 may couple each other in electrical communication such that electric charge generated by nanomaterial of the nanotube structures 404 may collect on the interconnect 408 and the conductive nature of the interconnect 408 may then transfer the electric charge to another portion, or part, of the substrate 402 and/or the orthopedic prosthesis 100.

In some embodiments, the interconnect 408 may serve as an electric charge storage device. The interconnect 408 may be of a variety of forms including a bioabsorbable/biodegradable material, sheet structure such as graphene and/or a coating. The interconnect 408 may be positioned on the implant substrate surface and/or between nanotubes of a nanomaterial and the substrate 402, in between adjacent nanotubes, adjacent to a bioactive material, and/or combinations thereof. Further, the interconnect 408 can be located on an implant surface and/or adjacent to, and/or in communication with the Implant.

Figure 5:
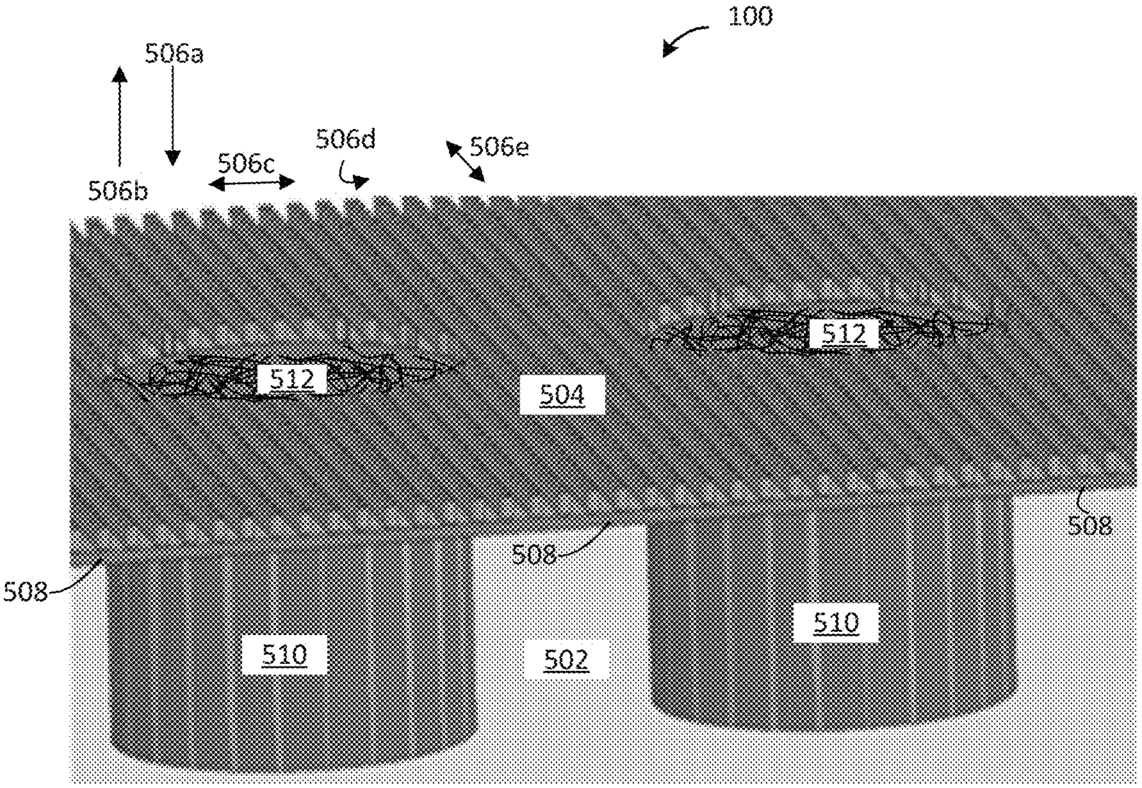
FIG. 5 is a perspective view of a substrate with nanotube structures, an interconnect, and one or more voids, according to another embodiment of the present disclosure.

FIG. 5 is a perspective view of a portion of an orthopedic prosthesis 100 comprising a substrate 502, nanotube structures 504, an interconnect 508, and one or more voids 510 or openings, according to another embodiment of the present disclosure. The substrate 502 is shown as transparent in order to show the internal structures of the orthopedic prosthesis 100. Mechanical forces 506*a*, 506*b*, 506*c*, 506*d*, and 506*e* may act on the orthopedic prosthesis 100 similar those described in relation to FIG. 2. The one or more voids 510 may serve to store electric charge for subsequent use to promote bone growth. The one or more voids 510 may include or may be packed with, a biocompatible charge storing material, biodegradable charge storing material, bioabsorbable charge storing material, and/or the like. A charge storing material 512 may serve to hold electric charge until a later point in time. In some embodiments, external forces may cause the stored electric charge to be utilized to promote bone growth. Examples of charge storing material 512 may include, but are not limited to carbon fibers, carbon yarns, buckyballs, fullerenes, etc. In this manner, the charge storing material 512 may produce a synthetic allograft by holding sufficient electric charge.

In some embodiments, the one or more voids 510 may extend through the entire substrate, extend to a predefined depth within the substrate 502 from an outer surface of the substrate 502, or may comprise an internal structure of the substrate 502 or implant, and/or combinations thereof. The charge storing material 512 may be utilized as void fillers and/or positioned within the voids.

In some embodiments, the one or more voids 510 and/or contents of the one or more voids 510 may be electrically insulated from, or disconnected from, the interconnect 508 and/or the nanotube structures 504. In this manner, electric charge stored in the one or more voids 510 or on or within contents of the one or more voids 510 may remain within the voids 510. In some embodiments, to maintain electrical isolation in view of body fluids of a patient, a biodegradable insulation layer (e.g., biodegradable polymer coating) a may be applied over the voids 510 and/or between contents of the voids 510 and the interconnect 508.

In some embodiments, at least one of the one or more voids 510 and/or contents of the one or more voids 510 may be in electrical communication with the interconnect 508 and/or the nanotube structures 504. In this manner, electric charge stored in the one or more voids 510 or on or within contents of the one or more voids 510 may move freely between the one or more voids 510 and another portion of substrate 502 or a structure that includes the substrate 502.

Figure 6A:
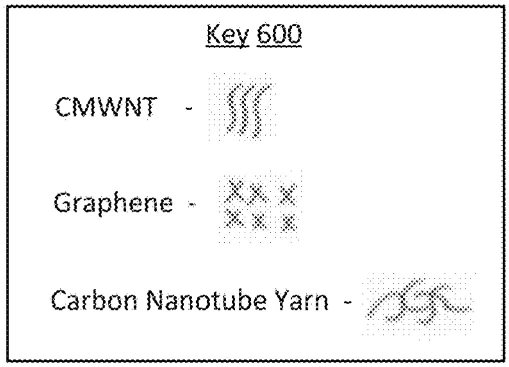
FIG. 6A is a cross-sectional view of an orthopedic prosthesis, according to an embodiment of the present disclosure.
Figure 6A:
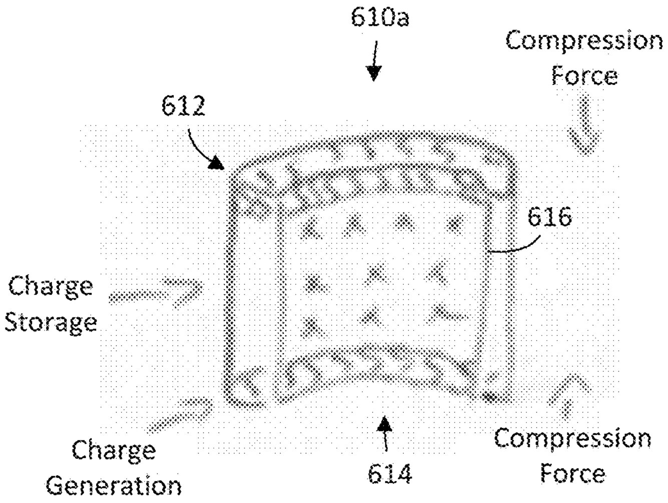
Figure 6B:
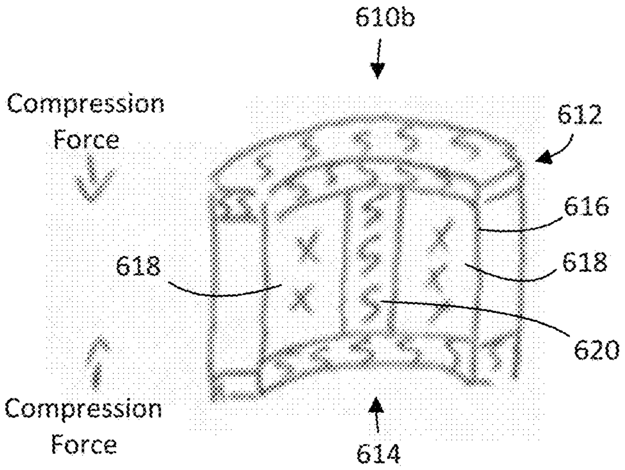
FIG. 6B is a cross-sectional view of an orthopedic prosthesis, according to another embodiment of the present disclosure.
Figure 7A:
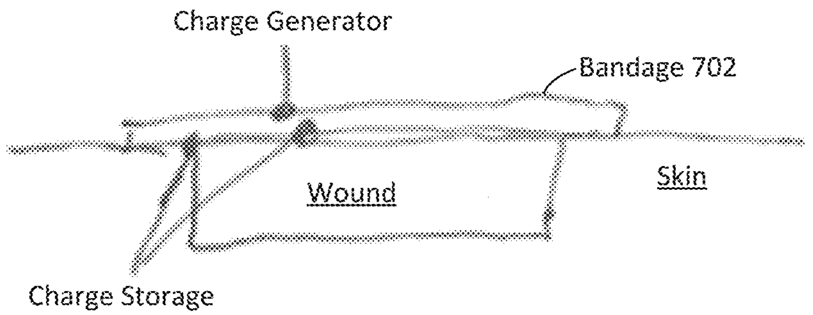
FIG. 7A is a cross-sectional side view of a soft tissue device or bandage applied to a wound, according to another embodiment of the present disclosure.
Figure 7B:
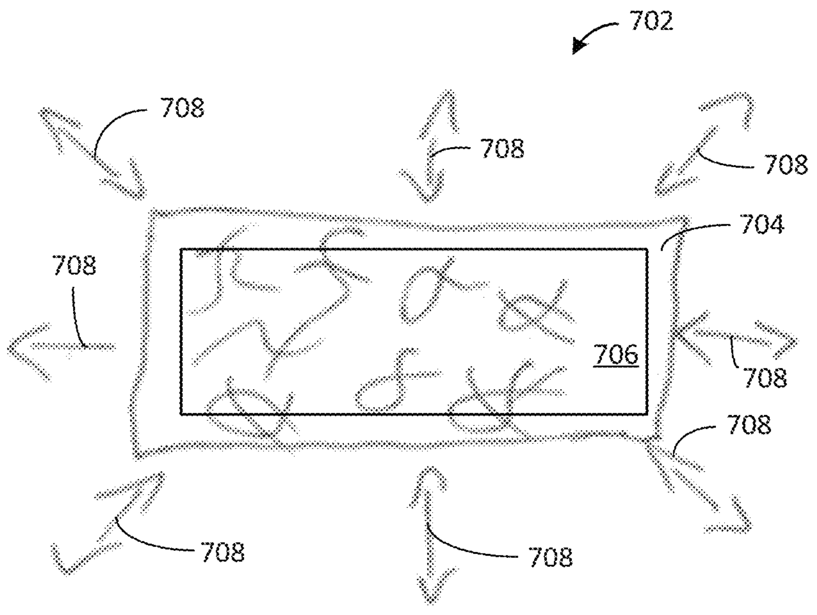
FIG. 7B is a top view of the soft tissue device of FIG. 7A.

FIGS. 6A, 6B, and 7B make use of a key 600 that identifies which molecule, compound, or material, is represented by which pattern shown in the key 600. The three example molecule, compound, or materials utilized in the illustrations include: Carbon Multi-Walled Nanotubes (CMWNTs), Graphene, and Carbon Nanotube Yarns. However, those of skill in the art will recognize that a variety of other materials can be utilized with the embodiments presented in this disclosure. In this manner, previously discussed materials and structures may be utilized interchangeably with the examples illustrated in the key 600 and in FIGS. 6A, 6B, and 7B. For example, in some embodiments single walled carbon nanotubes (SWCNTs) may be utilized in the embodiments illustrated in FIGS. 6A, 6B, 7A, and 7B.

FIG. 6A is a cross-sectional view of an orthopedic prosthesis 610*a*, according to an embodiment of the present disclosure. In some embodiments, the orthopedic prosthesis 610*a* may comprise a fusion cage, as only one of a variety of applications of the concepts and aspects disclosed in the present disclosure. FIG. 6A illustrates an orthopedic prosthesis 610*a* that includes a substrate shaped to form a body of the orthopedic prosthesis 610*a*. The orthopedic prosthesis 610*a* may include a superior end 612 and an inferior end 614. In some embodiments, the superior end 612 and/or the inferior end 614 may include carbon multi-walled nanotubes (CMWNTs) on their surfaces, which may comprise bone-facing surfaces.

The orthopedic prosthesis 610*a* may also include an interior surface or interior wall 616. In some embodiments, the interior wall 616 may include an interconnect (such as graphene, as one non-limiting example) that may extend from the superior end 612 to the inferior end 614. In some embodiments, the graphene may be applied as a layer, a sheet, or a coating. As previously discussed, the interconnect may serve as a conductor of electric charge between the superior end 612 and the inferior end 614, as well as charge storage device so electric charge can build up and reside on the interconnect. In this manner, the interconnect can even out or balance the electric charge between the superior end 612 and the inferior end 614.

When the orthopedic prosthesis 610*a* is installed between two bones, particularly load bearing bones, the CMWNTs may experience mechanical forces (e.g., cyclic compression forces, etc.) as the patient moves and the CMWNTs may generate an electrical charge in response thereto. The interconnect may be in electrical communication with the superior end 612 and/or the inferior end 614 such that the electric charge can move between each end. Once the electric charge is equalized, the electric charge may start to build up on the interconnect and/or within the two ends of the orthopedic prosthesis 610*a*.

In some embodiments, the interconnect may comprise a planar sheet and thus may function like a capacitor and collect more and more charge. If the superior end 612 and/or the inferior end 614 are electrically isolated (e.g., not electrically grounded), the built up charge on the interconnect may transfer electric charge from either end to the other end, or to an internal surface, such as a surface that faces bone graft material placed within a void 112 of the orthopedic prosthesis 610*a*. In some embodiments, the bone graft material placed within the void 112 may comprise nanomaterials (such as carbon nanotubes, carbon yarns, etc.) such that electric charge may be stored in these nanomaterials within the void 112.

In some embodiments, the electric charge may stay on a surface of the superior end 612, the inferior end 614, and/or the interior wall 616. In some embodiments, the CMWNTs and graphene nanosheet may be configured such that positive electric charge collects at the ends and negative electric charge collects on the surface of the interior wall 616. Such a charge distribution may promote more bone in-growth within the orthopedic prosthesis 610*a*. Electric charge on the surface of the superior end 612, the inferior end 614, and/or the interior wall 616 may be utilized in the generation of bone or may be dissipated into the cells and/or bone graft material contacting the surface of the superior end 612, the inferior end 614, and/or the interior wall 616.

In this manner, the CMWNT's on either end may generate charge and the interconnect may transfer the electric charge within the orthopedic prosthesis 610*a* to promote bone in-growth inside the orthopedic prosthesis 610*a*. In addition, the interconnect can store and collect electric charge for use over time to promote bone growth.

FIG. 6B is a cross-sectional view of an orthopedic prosthesis 610*b*, according to another embodiment of the present disclosure, similar to the embodiment of FIG. 6A with like parts having like numbering. An interior wall 616 of the orthopedic prosthesis 610*b* may include one or more columns 618 of graphene and one or more columns 620 of a nanomaterial such as CMWNTs. Of course, various combinations of columns and patterns may be utilized to provide one or more interconnects between the superior end 612, the inferior end 614, and the interior wall 616. In some embodiments, the graphene and/or the CMWNTs may be applied as coatings to form the one or more columns 618 and the one or more columns 620.

FIGS. 7A and 7B illustrate a soft tissue device or bandage 702 applied to a wound of a patient, according to another embodiment of the present disclosure. FIG. 7A is a cross-sectional side view of the bandage 702 applied to the wound on the skin of a patient, and FIG. 7B is a top view of the bandage 702 comprising a flexible mesh 706 and/or a pliable sheet 704.

In some embodiments, the bandage 702 can apply the piezoelectric properties of nanomaterials discussed or contemplated herein to generate an electric charge to promote healing of the wound in the soft tissue.

In some embodiments, the flexible mesh 706 may include a plurality of piezoelectric fibers interwoven with each other to form the flexible mesh 706.

In some embodiments, a tissue-facing surface of the flexible mesh 706 may be in electrical communication with the wound of the patient.

In some embodiments, the flexible mesh 706 may be couplable to the skin of the patient proximate the wound.

In some embodiments, the plurality of piezoelectric fibers may be configured to generate an electric charge in response to at least one mechanical force applied to the plurality of piezoelectric fibers via movement of the patient's skin relative to the flexible mesh 706.

In some embodiments, the tissue-facing surface of the flexible mesh may be configured to transmit the electric charge to the wound to stimulate tissue growth and promote healing of the wound.

In some embodiments, the pliable sheet 704 and the flexible mesh 706 may be coupled to each other, and the pliable sheet 704 may also be coupled to the skin of the patient. In this manner, when the patient (or the patient's skin) moves, mechanical forces 708 may be transferred to the pliable sheet 704 and the flexible mesh 706. These mechanical forces 708 may tension, relaxation, and/or compression forces resulting from patient movement.

In some embodiments, the flexible mesh 706 may include a plurality of nanomaterial fibers and/or yarns, such as carbon fiber yarns, nanotube fibers, etc. These nanomaterial fibers may experience the mechanical forces 708 and generate an electric charge in response thereto which may then be provided to the wound to promote healing of the soft tissue. In this manner, carbon fiber arrays may be utilized in bandages and/or dressings where tension and relaxation due to the body movement can generate small electrical fields around a soft tissue wound. Enhanced wound healing may occur via application of such electrical fields, resulting in decreased infection rates for soft tissue wounds.

In some embodiments, the flexible mesh 706 and/or the pliable sheet 704 may also include an interconnect such as a sheet of graphene that may connect the flexible mesh 706 or an internal part of the flexible mesh 706 and/or the pliable sheet 704 to an external portion and/or a portion of the wound, or vice versa. For example, the interconnect may be utilized to transfer electric charge to an interior section of the wound to promote healing. In this manner, the interconnect can be used to transfer a generated electric charge and/or store a generated electric charge, as previously discussed herein.

Any procedures or methods disclosed herein may comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment. This method of disclosure is also not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, components that are removably and/or non-removably coupled with each other, components that are functionally coupled to each other through one or more intermediary components, etc. The term "abutting" refers to items that may be in direct physical contact with each other, although the items may not necessarily be attached together. The phrase "fluid communication" refers to two or more features that are connected such that a fluid within one feature is able to pass into another feature. As defined herein the term "substantially" means within +/−30% of a target value, measurement, or desired characteristic.

While specific embodiments and applications of the present disclosure have been illustrated and described, it is to be understood that the scope of the present disclosure is not limited to the precise configurations and components disclosed herein. Various modifications, changes, and variations which will be apparent to those skilled in the art may be made in the arrangement, operation, and details of the devices, systems, and/or methods disclosed herein.

What is claimed is:

1. An orthopedic prosthesis for stimulating bone growth comprising:
- a substrate comprising:
  - at least one bone-facing surface; and
  - at least one internal surface;
- at least one piezoelectric nanostructure coupled to the at least one bone-facing surface of the substrate;
- at least one charge storing material placed within the orthopedic prosthesis proximate the at least one internal surface; and
- an interconnect in electrical communication with the at least one piezoelectric nanostructure and the charge storing material, wherein:
- the at least one piezoelectric nanostructure is configured to generate an electric charge in response to at least one mechanical force applied to the at least one piezoelectric nanostructure; and
- the interconnect is configured to transfer the electric charge to the at least one charge storing material to promote bone in-growth within the orthopedic prosthesis and/or on the at least one bone-facing surface.

2. The orthopedic prosthesis of claim 1, wherein the at least one piezoelectric nanostructure comprises at least one nanotube.

3. The orthopedic prosthesis of claim 2, wherein the at least one nanotube comprises at least one carbon nanotube.

4. The orthopedic prosthesis of claim 2, wherein the at least one nanotube comprises a plurality of nanotubes projecting from the at least one bone-facing surface and oriented substantially parallel with each other.

5. The orthopedic prosthesis of claim 1, wherein the interconnect comprises a graphene nanosheet.

6. The orthopedic prosthesis of claim 1, wherein the at least one charge storing material comprises carbon.

7. The orthopedic prosthesis of claim 1, wherein the orthopedic prosthesis is configured to experience the at least one mechanical force while the orthopedic prosthesis is implanted within a patient.

8. An orthopedic prosthesis for stimulating bone growth comprising:
- a substrate comprising at least one bone-facing surface;
- a first piezoelectric nanostructure coupled to the at least one bone-facing surface at a first location;
- a second piezoelectric nanostructure coupled to the at least one bone-facing surface at a second location; and
- a conductor comprising a graphene nanosheet electrically coupled with the first piezoelectric nanostructure and the second piezoelectric nanostructure, wherein:
- the first piezoelectric nanostructure is configured to generate a first electric charge in response to a first mechanical force applied to the first piezoelectric nanostructure;

the second piezoelectric nanostructure is configured to generate a second electric charge in response to a second mechanical force applied to the second piezoelectric nanostructure; and the conductor is configured to:

transfer the first electric charge to the second piezoelectric nanostructure; and transfer the second electric charge to the first piezoelectric nanostructure to promote bone growth on at least one of the first location and the second location of the at least one bone-facing surface.

9. The orthopedic prosthesis of claim 8, wherein at least one of the first piezoelectric nanostructure and the second piezoelectric nanostructure comprises a nanotube.

10. The orthopedic prosthesis of claim 9, wherein the nanotube comprises a carbon nanotube.

11. The orthopedic prosthesis of claim 9, wherein the nanotube comprises a plurality of nanotubes projecting from the at least one bone-facing surface and oriented substantially parallel with each other.

12. The orthopedic prosthesis of claim 8, wherein the orthopedic prosthesis is configured to experience at least one mechanical force while the orthopedic prosthesis is implanted within a patient.

13. An orthopedic prosthesis for stimulating bone growth comprising:

a substrate comprising:

a first bone-facing surface; and a second bone-facing surface, opposite the first bone-facing surface;

a first piezoelectric nanostructure coupled to the first bone-facing surface;

a second piezoelectric nanostructure coupled to the second bone-facing surface; and at least one interconnect comprising a graphene nanosheet in electrical communication with at least one of the first piezoelectric nanostructure and the second piezoelectric nanostructure, wherein:

the first piezoelectric nanostructure is configured to generate a first electric charge in response to a compression force applied to the first piezoelectric nanostructure;

the second piezoelectric nanostructure is configured to generate a second electric charge in response to the compression force applied to the second piezoelectric nanostructure; and the at least one interconnect is configured to transmit at least one of the first electric charge and the second electric charge to promote bone growth on at least one of the first bone-facing surface and the second bone-facing surface.

14. The orthopedic prosthesis of claim 13, wherein at least one of the first piezoelectric nanostructure and the second piezoelectric nanostructure comprises a nanotube.

15. The orthopedic prosthesis of claim 14, wherein the nanotube comprises a carbon nanotube.

16. The orthopedic prosthesis of claim 14, wherein the nanotube comprises a plurality of nanotubes oriented substantially parallel with each other and projecting from at least one of the first bone-facing surface and the second bone-facing surface.

17. The orthopedic prosthesis of claim 13, wherein the orthopedic prosthesis is configured to experience the compression force while the orthopedic prosthesis is implanted within a patient.

18. The orthopedic prosthesis of claim 13, wherein:

the at least one interconnect is in electrical communication with the first piezoelectric nanostructure coupled to the first bone-facing surface and the second piezoelectric nanostructure coupled to the second bone-facing surface;

the at least one interconnect extends between the first bone-facing surface and the second bone-facing surface; and the at least one interconnect is configured to transmit at least one of the first electric charge and the second electric charge between the first bone-facing surface and the second bone-facing surface to promote bone growth on at least one of the first bone-facing surface and the second bone-facing surface.

* * * * *